T861001

DEFENSIVE PUBLICATION

UNITED STATES PATENT OFFICE

Published at the request of the applicant or owner in accordance with the Notice of Apr. 11, 1968, 849 O.G. 1221. Identification is by serial number of the application and the heading indicates the number of pages of specification, including claims, and of sheets of drawing contained in the application as originally filed. The file of this application is available to the public for inspection; reproduction may be purchased for 30 cents per sheet.

Applications published under the Defensive Publication Program have not been examined as to the merits of alleged invention. The Patent Office makes no assertion as to the novelty of the disclosed subject matter.

PUBLISHED APRIL 1, 1969

861 O.G. 17

628,785

ESTERS AND METHOD OF PRODUCTION

Roy B. Duke, Jr., Smyrna, Ga., and Milton A. Perry, Longview, Tex., assignors to Eastman Kodak Company, Rochester, N.Y., a corporation of New Jersey

Continuation of application Ser. No. 444,331, Mar. 31, 1965. This application Apr. 5, 1967. Published Apr. 1, 1969

Class 260—345.8

1 Sheet Drawing. 18 Pages Specification

Alkyl methacrylate and neopentyl glycol are prepared by a process comprising the non-catalytic condensation of a heterocyclic aldehyde with certain hydroxy aldehydes to obtain a corresponding monohydroxy ester. The monohydroxy ester is contacted with an alcohol in the presence of an alcoholysis catalyst to obtain the desired 2,2-dialkyl-1,3-propanediol and an alkyl ester of an unsaturated heterocyclic organic acid. The ester is then pyrolyzed to form the desired alkyl methacrylate.

T861001
April 1, 1969 R. B. DUKE, JR., ETAL DEF. PUB.
ESTERS AND METHOD OF PRODUCTION SN - 628785
Original Filed March 31, 1965
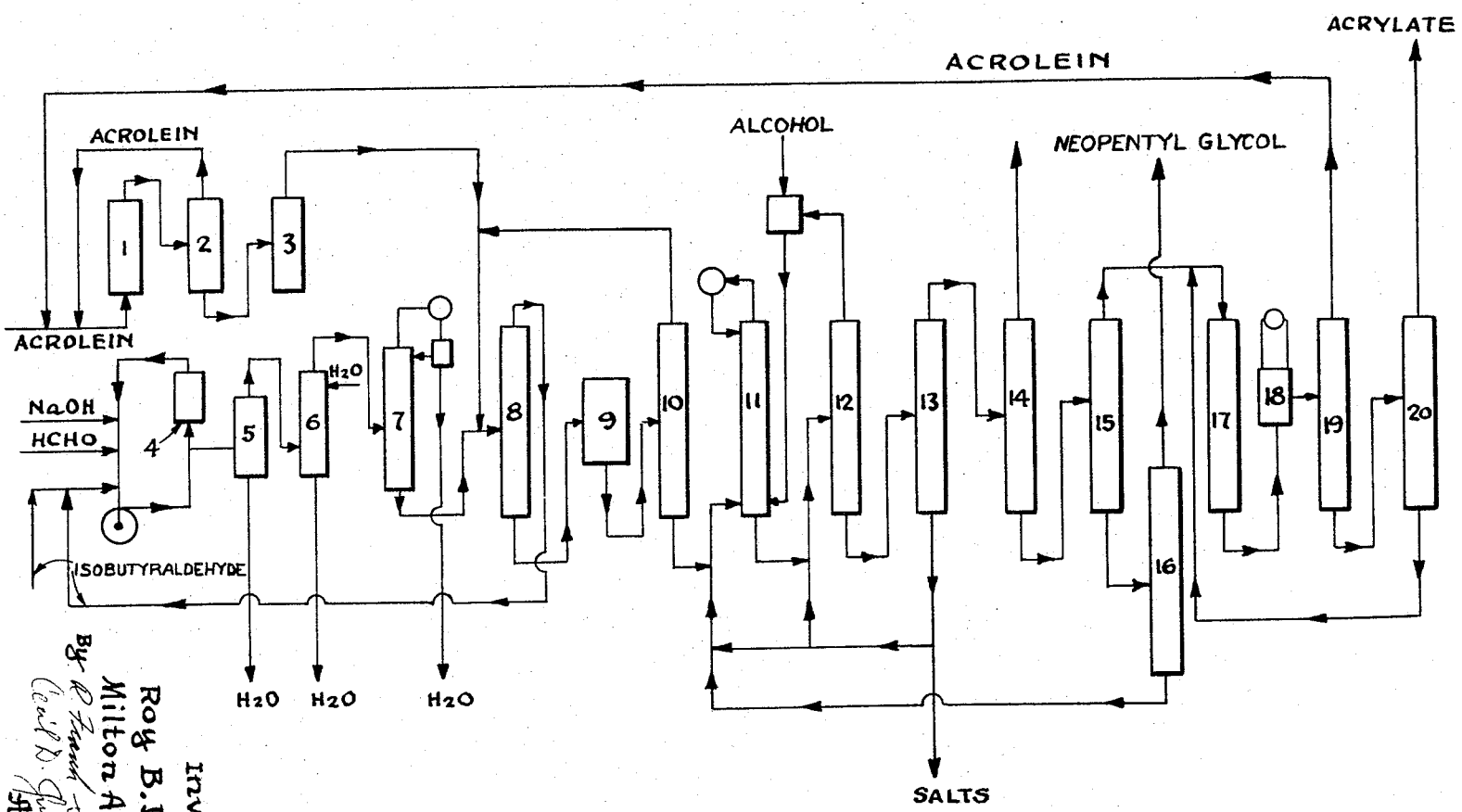
Inventors
Roy B. Duke, Jr.
Milton A. Perry
By R. Frank Smith
Cecil D. Quillen
Attorneys